US00PP36586P2

(12) United States Plant Patent
Clark et al.

(10) Patent No.: US PP36,586 P2
(45) Date of Patent: Apr. 8, 2025

(54) NECTARINE TREE NAMED 'A-662CN'

(50) Latin Name: *Prunus persica*
Varietal Denomination: A-662CN

(71) Applicant: THE BOARD OF TRUSTEES OF THE UNIVERSITY OF ARKANSAS, Little Rock, AR (US)

(72) Inventors: John R. Clark, Fayetteville, AR (US); Margaret L. Worthington, Fayetteville, AR (US); James Moore, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 18/831,156

(22) Filed: Aug. 20, 2024

(51) Int. Cl.
*A01H 5/08* (2018.01)
*A01H 6/74* (2018.01)

(52) U.S. Cl.
USPC ..... Plt./187

(58) Field of Classification Search
USPC ..... Plt./156, 180, 187
See application file for complete search history.

(56) References Cited

U.S. PATENT DOCUMENTS

| | | | |
|---|---|---|---|
| PP12,620 | P2 | 5/2002 | Clark et al. |
| PP12,622 | P2 | 5/2002 | Clark et al. |
| PP12,641 | P2 | 5/2002 | Clark et al. |
| PP15,159 | P3 | 9/2004 | Clark et al. |
| PP17,742 | P3 | 5/2007 | Clark et al. |
| PP17,911 | P3 | 8/2007 | Clark et al. |
| PP22,464 | P3 | 1/2012 | Clark et al. |
| PP26,367 | P3 | 2/2016 | Clark et al. |
| PP26,402 | P3 | 2/2016 | Clark et al. |
| PP26,920 | P3 | 7/2016 | Clark |
| PP31,192 | P2 | 12/2019 | Worthington et al. |
| PP35,017 | P2 | 2/2023 | Clark et al. |
| PP35,897 | P3 | 6/2024 | Clark et al. |

OTHER PUBLICATIONS

Beckman, T. G., et al. "Peach tree short life." Southeastern peach growers handbook. University of Georgia, College of Agricultural and Environmental Sciences. Cooperative Extension Service, Athens (2004): 199-205.

Ghiani, A., et al. "Melting of 'Big Top' nectarine fruit: Some physiological, biochemical, and molecular aspects." Journal of the American Society for Horticultural Science 136.1 (2011): 61-68.

Plant Variety Protection 9400013. Peach BY520-9. Issued Jun. 14, 2001.

Sandefur, P. et al. "Peach texture." Horticultural Reviews vol. 41 (2013): 241-302.

Vauterin, L., et al. "Reclassification of xanthomonas." International Journal of Systematic and Evolutionary Microbiology 45.3 (1995): 472-489.

Worthington, M. and Clark, J.R. Peach breeding at the University of Arkansas. Acta Hortic. (2021). 1304, 21-28.

*Primary Examiner* — Karen M Redden
(74) *Attorney, Agent, or Firm* — Quarles & Brady, LLP

(57) ABSTRACT

A new and distinct nectarine tree named 'A-662CN' which originated from a hand-pollinated cross of 'A-421CN' nectarine (female parent; unreleased breeding selection) x 'A-334CN' nectarine (male parent; unreleased breeding selection) made in 1993 is described. This new nectarine tree cultivar can be distinguished by its yellow, standard-acid, firm flesh, early-season ripening, high soluble solids content, outstanding flavor, good postharvest performance, and moderate tolerance to bacterial spot.

3 Drawing Sheets

Latin name: *Prunus persica.*
Varietal denomination: 'A-662CN'.

BACKGROUND

A new and distinct nectarine tree named 'A-662CN' is described herein. The new cultivar originated from a hand-pollinated cross of 'A-421CN' nectarine (female parent; unreleased breeding selection) x 'A-334CN' nectarine (male parent; unreleased breeding selection) made in 1993. The seeds resulting from this controlled hybridization were germinated and grown in a greenhouse during the winter of 1993-94 and were planted in an orchard near Clarksville, Arkansas. This new cultivar was selected in 1997 for its potential as a fresh-market nectarine in Arkansas and the mid- to upper-southern United States. 'A-662CN' can be distinguished by its yellow, standard-acid, firm flesh, early-season ripening, high soluble solids content, outstanding flavor, good postharvest performance, and moderate tolerance to bacterial spot.

SUMMARY OF THE INVENTION

The new and distinct nectarine cultivar originated from a hand-pollinated cross of 'A-421CN' nectarine (female parent; unreleased breeding selection) x 'A-334CN' nectarine (male parent; unreleased breeding selection) made in 1993 near Clarksville, AR. The seeds resulting from this controlled hybridization were germinated in a greenhouse during the winter of 1993-94 and planted in a field near Clarksville, AR. The seedlings fruited during the summer of 1997, and one nectarine seedling, designated 'A-662CN', was selected for its yellow, standard-acid, firm flesh, early-season ripening, high soluble solids content, outstanding flavor, good postharvest performance, and moderate tolerance to bacterial spot.

The original plant selection was propagated asexually during 1993 at the above-noted location by budding onto the standard peach rootstock cultivar 'Guardian'® (BY520-9;

U.S. Plant Variety Protection No. 9,400,013) and a test plot of two plants was established. Subsequently, a larger test planting was established with asexually multiplied plants near Clarksville, Arkansas in 2016 and 2019. Propagation for the larger replicated trials were also budded onto the standard peach rootstock cultivar 'Guardian'® from buds collected at the original Clarksville, AR test plot. No incompatibility with peach rootstocks has occurred following budding. During all asexual multiplication, the characteristics of the original plant have been maintained and no aberrant phenotypes have appeared.

The new cultivar has been named 'A-662CN'.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
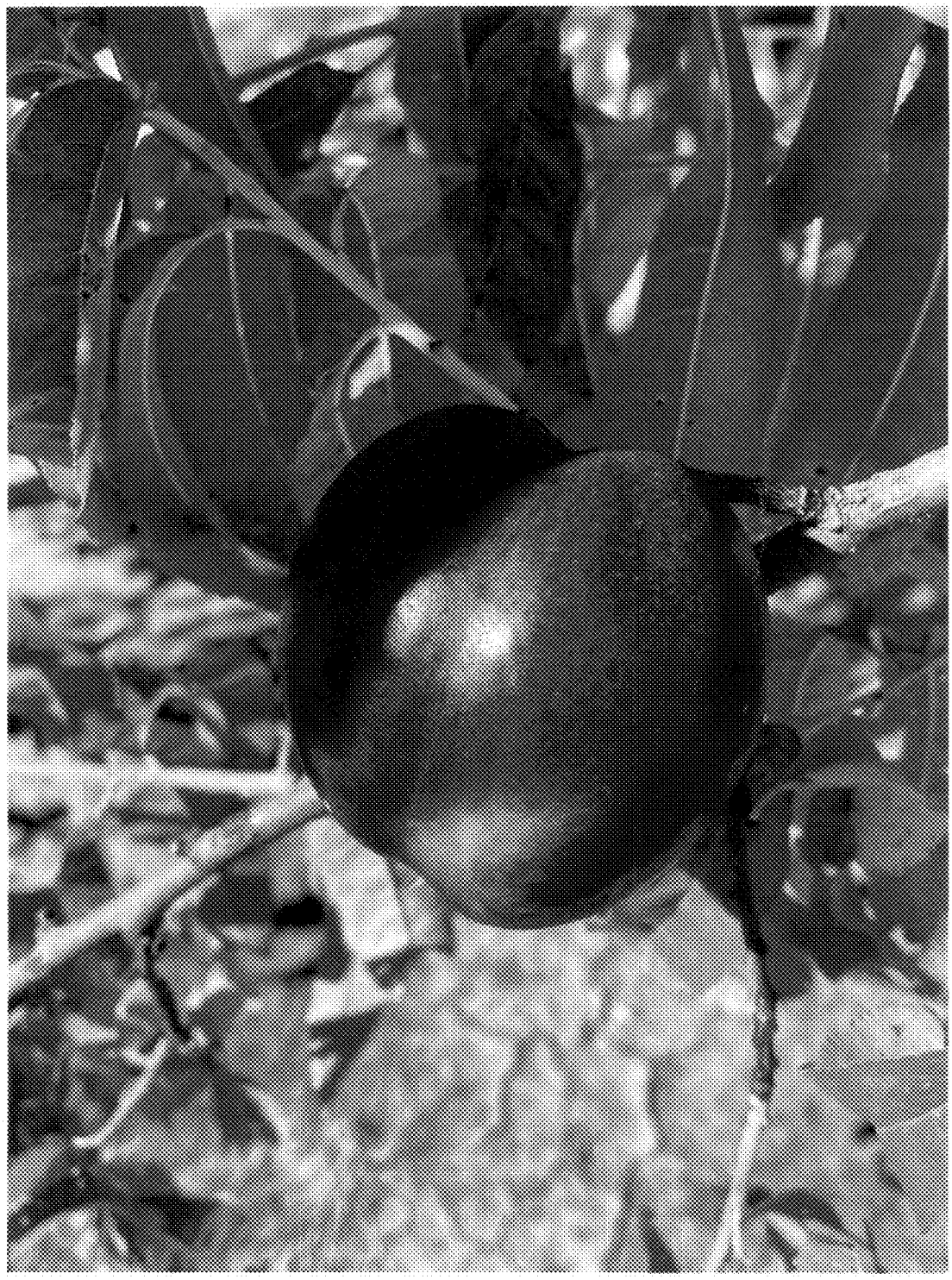
FIG. 1 is a photograph of mature fruit from an 'A-662CN' tree at fifteen years of age.
Figure 2:
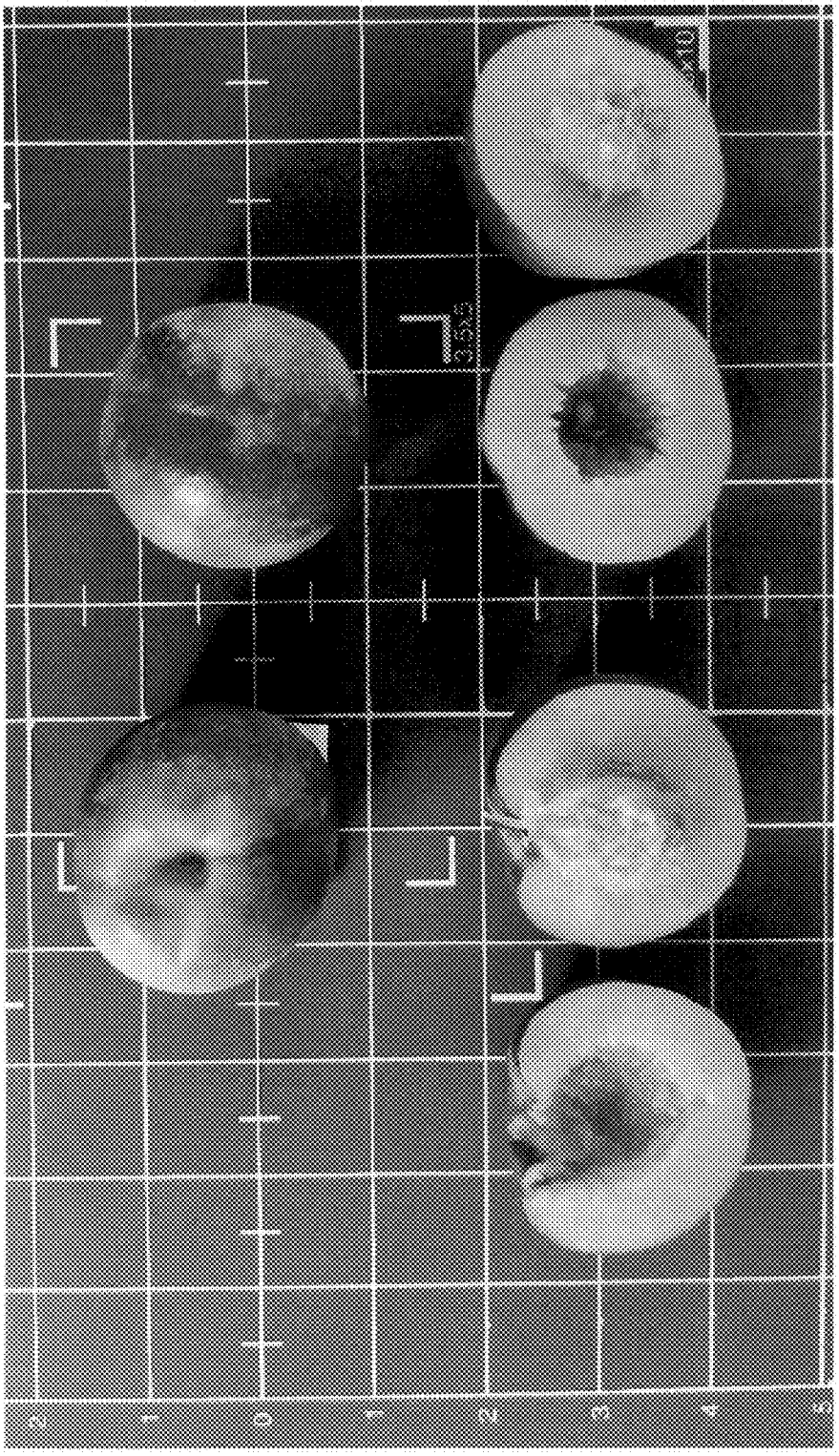
FIG. 2 is a photograph of a whole (left), latitudinally cut (right, top), and longitudinally cut (right, bottom) fruit of 'A-662CN' at maturity collected from a tree at fifteen years of age.
Figure 3:
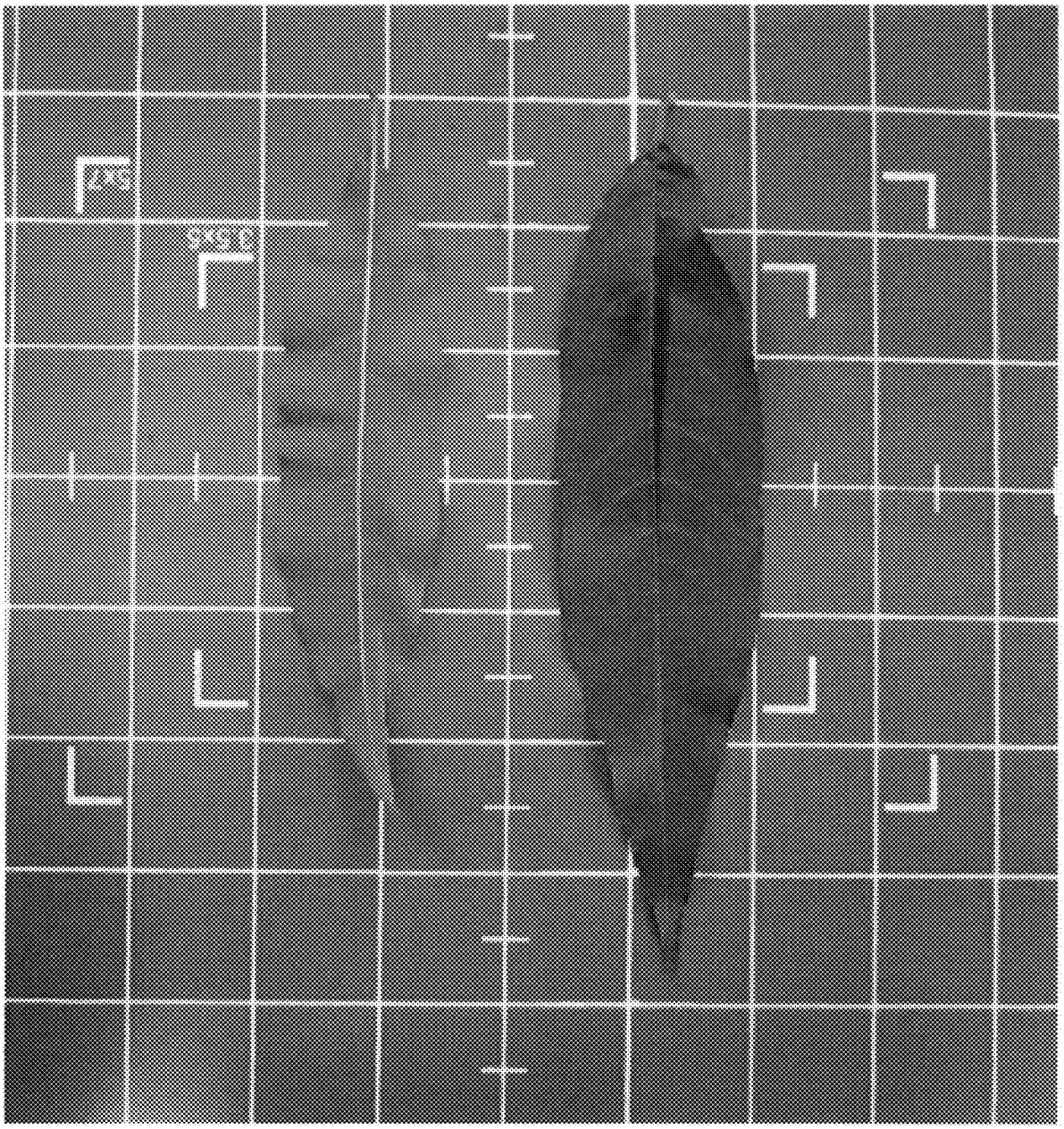
FIG. 3 is a photograph of the abaxial (left) and adaxial (right) surfaces of mature 'A-662CN' leaves collected from a tree at fifteen years of age.

'A-662CN' and both of its parents, 'A-421CN' and 'A-334CN', produce clingstone, non- melting flesh fruit with standard acidity. Both aforementioned parents and the new cultivar are of the genus and species *Prunus persica*. Plants and fruit of this new cultivar also differ phenotypically from its parents. 'A-662CN' differs from its male parent, 'A-421CN', in that 'A-421CN' had high occurrence of fruit crack after rain events, and 'A-662CN' generally maintains good quality after rain. Fruit from 'A-421CN' also was prone to having a pronounced pointed (mucron) tip, which is an undesirable trait for fresh-market nectarines, whereas 'A-662CN' generally has well-formed, rounded fruit. 'A-662CN' differs from the female parent, 'A-334CN', in that 'A-662CN' received higher and more consistent breeder ratings for fruit flavor and appearance. The average ripening date of 'A-662CN' in Clarksville, AR, is one week earlier than 'Amoore Sweet' (U.S. Plant Pat. No. 26,367) and 'Bowden' (U.S. Plant Pat. No. 26,402), similar to 'Bradley' (U.S. Plant Pat. No. 12,620), a few days to one week later than 'Arrington' (U.S. Plant Pat. No. 12,641), and typically about two weeks later than 'Westbrook' (U.S. Plant Pat. No. 12,622).

Trees of the new cultivar are vigorous, productive, standard in size, well-branched and symmetrical with a semi-upright growth habit, comparable to other nectarine trees. Tree size and form is comparable to that of the 'Amoore Sweet' and 'Effie' cultivars in west-central Arkansas. Trees express a moderate level of resistance to both foliar and fruit infection of bacterial spot [*Xanthomonas campestris* pv. *pruni* (Smith) Dye]. The new cultivar blooms in the spring on approximately the same date as 'Bradley', four days later than 'Amoore Sweet', and about one day later than 'Arrington', 'Bowden', 'Effie' (U.S. Plant Pat. No. 31,192), and 'Westbrook'. No winter cold injury was observed on wood or buds of the new cultivar in Arkansas tests between 2012 and 2020 where minimum temperatures reached 2° F. (−17° C.) during evaluation. However, significant bud damage was observed in spring 2021 after low temperatures reached −15° F. (−26° C.) in February 2021. Chilling requirement to break dormancy is estimated to be 800 hours below 45° F. (7° C.).

Fruit of the new cultivar ripens mid-early-season, averaging one to two weeks later than 'Westbrook', four days later than 'Arrington', and two to three weeks earlier than 'Effie' reference cultivars. The average first ripening date is July 1 in west-central Arkansas (Clarksville). Fruit yields have been fair and are comparable to the nectarine cultivar 'Arrington'.

The fruit is round in shape. Fruits are attractive with an average 63% light red blush. The average fruit finish rating of 'A-662CN' was 7.0, higher than the comparison cultivars 'Amoore Sweet', 'Bowden', 'Effie', and 'Westbrook'. The flesh of the fruit is yellow in color with no red flecking or discoloration. Flesh is of the non-melting type, crisp at early ripening and remains crisp fully ripe. The fruit is a clingstone, and the flesh does not separate cleanly from the pit. Fruit size is small to medium, averaging 145 g, slightly larger than the early-ripening comparison cultivars 'Arrington' (133 g) and 'Westbrook' (124 g), and smaller than 'Amoore Sweet' (166 g), 'Bowden' (163 g), 'Bradley' (181 g), and 'Effie' (160 g). The fresh fruit has excellent yellow nectarine flavor and was rated highly in evaluations. Fruits average 14.9% soluble solids, higher than 'Amoore Sweet', 'Bowden', 'Bradley', and 'Westbrook', but lower than 'Effie'. The acidity level of 'A-662CN' was 0.67-0.81% malic acid, which was higher than 'Amoore Sweet' and lower than 'Westbrook' on average. The overall flavor of 'A-662CN' is sweet with standard acidity and noteworthy tropical-like aromatics.

The following is a detailed description of the botanical and pomological characteristics of the subject nectarine. Color data are presented in Royal Horticultural Society Colour Chart designations (1986, $2^{nd}$ edition). Where dimensions, sizes, colors and other characteristics are given, it is to be understood that such characteristics are approximations of averages set forth as. accurately as practical.

Plants used for botanical data were fifteen years old and grown on a fine sandy loam soil with trickle irrigation near Clarksville, AR. Trees were trained to an open-center training system and dormant pruned annually. The exception to this is that yield data was collected on trees four years old and trained to a perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were made to the trees. No bactericides were applied to plantings during testing before fall 2018. Beginning in fall 2018, copper was applied twice annually during dormancy and delayed dormancy to reduce inoculum of bacterial canker (*Pseudomonas syringae* pv. *persicae*) and bacterial spot (*Xanthomonas arboricola* pv. *pruni*). The descriptions reported herein are from specimens grown near Clarksville, AR.

Plant:

*Size*.—Mature trees (six years of age) average 3.9 m in height and 4.4 m in spread or width, and with a semi-upright growth habit, as grown on 'Guardian'®

BY520-9 rootstock using an open-center training system commonly used on nectarines.

*Growth*.—Vigorous, symmetrical form, good canopy development.

*Productivity*.—Good productivity and consistent annual bearing. Fruit is produced on long shoots. Yields ranged from 8.7-11.9 kg/tree in replicated trials in west-central Arkansas.

Cold hardiness.—Wood and dormant buds hardy to 2° F. (−17° C.). Wood hardy to −15° F. (−26° C.), but approximately 75% of dormant buds were killed at this temperature.

*Disease resistance*.—Leaves and fruit moderately resistant but not immune to bacterial spot under growing conditions where bacterial spot infection is often very severe on susceptible genotypes. No bactericides were applied to plantings during testing before Fall 2018. Beginning in Fall 2018, copper was applied twice annually during dormancy and delayed dormancy to reduce inoculum of bacterial canker (*Pseudomonas syringae* pv. *persicae*) and bacterial spot (*Xanthomonas arboricola* pv. *pruni*). The average severity rating for leaf symptoms on 'A-662CN' observational trees was 1.8 out of 5, which was better than 'Westbrook' and comparable to 'Amoore Sweet', 'Arrington', 'Bradley', and 'Effie'. The percent of fruit with bacterial spot was rated 1.3 out of 5. The instant cultivar had lower bacterial spot disease occurrence ratings on fruit than 'Bowden' and rated similar to 'Amoore Sweet', 'Arrington', 'Effie' and 'Westbrook'. A commercial fungicide program was utilized in orchards throughout the development and evaluation of the instant cultivar, thus no resistance to brown rot (*Monilinia fructicola* (G. Winter) Honey) or scab (*Fusicladium carpophilum* (Thum.) Oudem), the other common diseases at Clarksville, AR, were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (*Synathedon pictipes* (Grote & Robinson)), and greater peach tree borer (*Synanthedon exitiosa* (Say)). Therefore, no insect resistance was determined in the testing of the instant cultivar.

Foliage/shoots/branches:

*Shoots*.—Texture: Smooth. Dormant-season shoot (one-year-old branch): length: 59.61 cm; diameter at base: 0.57 cm; diameter at midpoint: 0.46 cm; diameter at terminus: 0.38 cm; color: top: greyed-orange group (175B); bottom: green group (141D); spurs absent; mature shoot internode length: base: 0.60 cm; midpoint: 0.53 cm; terminus: 0.41 cm.

*Leaves*.—Simple, alternate, glabrous, petiolate, and deciduous; venation pattern: pinnate; shape base: oblique to acute; apex acuminate; overall shape lanceolate; margin: serrated with moderate undulation; young leaf color: abaxial — green group (149B); adaxial — green group (149A); anthocyanin not present on any portion of young leaves. Mature leaves v-shaped in cross-section; mature leaf size: length 12.0 cm; width at midpoint 2.96 cm. Length of blade tip: 3.46 mm. Leaf serrations 5.0/cm. Mature leaf color: abaxial — green group (137C); adaxial — green group (137A). Petiole length — mature leaf: 1.08 cm, petiole width: 1.41 mm; petiole texture: smooth no pubescence; petiole strength: strongly adheres to shoot; petiole color abaxial: green group (138B); petiole color adaxial: green group (138A). Nectarines: reniform shape, average of 2.0 per leaf, typically located at base of leaf blade, occasionally present on the petiole. Nectary: length: 1.34 mm; width 0.90 mm; nectary color: yellow-green group (150C). Stipule length: 0.78 cm; stipule width 0.96 mm. Stipule texture: smooth on abaxial and adaxial surfaces, margins serrated. Stipule color: abaxial — yellow-green group (144B); adaxial — yellow-green group (144B).

*Buds*.—Number of leaf buds per 15 cm: 8.00, evenly distributed along the shoot. Number of flower buds per 15 cm from terminal: 13.63.

Bark (of mature trunk of tree):

*Color*.—Greyed-orange group (166A).

*Texture*.—Rough; no pubescence; lenticel density: 6 per $cm^2$; lenticel color: greyed-orange group (165B).

Trunk:

*Diameter*.—33.27 cm (at 25 cm above ground level).

Flowers: Bloom occurs prior to vegetative bud break; typically, 1-2 individual flowers at a single node; perfect; self-fertile.

*Floral buds*.—Shape: oval; color: greyed-green group (197C); length: 0.48 cm; diameter: 0.28 cm.

*Date of bloom*.—First, Julian 76 (March 16); Full, Julian 80 (March 20).

*Size*.—Diameter fully open: 2.06 cm; depth: 1.18 cm.

*Type*.—Non-showy.

*Color*.—Abaxial distal: red-purple group (73C); Abaxial proximal: red-purple group (73B); Adaxial distal: red-purple group (63C); Adaxial proximal: red-purple group (63B).

*Sepals*.—Number: 5; length: 4.49 mm; width: 3.58; overall shape: ovate; apex shape: rounded; margin: entire; abaxial color: green group (140B); adaxial color: red-purple group 60A.

*Petals*.—Number of petals per flower: 5; length: 12.33 mm; width: 7.26 mm; texture: smooth on both abaxial and adaxial surfaces. Shape: overall-elliptic; apex: obtuse; margin: smooth-entire; base: cuneate. Petal arrangement: petals touching to slightly overlapping.

*Pistil*.—Length: 1.81 cm. Color: stigma — green group (143B); style: yellow — green group (145B). Stigmas parallel with anthers; mostly at even length with anthers.

*Stamens*.—Average 32 per flower with pollen present, fertile and abundant. Anthers perpendicular with petals; at even length or slightly longer than petals.

*Pollen color*.—Yellow-orange group (20B).

*Ovaries*.—Smooth texture; Color: greyed-orange group (164A).

Fruit:

*Size*.—Medium, avg. 144 g. Diameter stem end 4.12 cm, equator 5.24 cm, blossom end 3.83 cm; length base to apex 5.00 cm.

*Shape*.—Round, symmetrical with occasional mucron tip <2.00 cm.

*Skin*.—Texture: smooth (nectarine); moderately glossy; attractive; ground color: yellow-orange group (23A); blush color: red group (46A); Blush description: near. solid to mottled blush covering about 63% of surface on average; no fruit lenticels present.

*Flesh*.—Color: yellow-orange group (22A) — uniform throughout fruit; clingstone; uniform non-melting texture.

*Pedicel length*.—2.92 mm.

*Pedicel diameter*.—3.33 mm.

*Pedicel color*.—Greyed-orange group (165A).

*Pedicel strength*.—Moderate to strong; holds on well.

*Average ripe date*.—June 30 (Julian 181) in west-central Arkansas; average last harvest date: July 10 (Julian 191) in west-central Arkansas.

*Soluble solids*.—15.1%.

*Fruit juice ph*.—3.68.

*Fruit juice titratable acidity*.—0.74% expressed as malic acid.

*Storage performance*.—Overall ranking for 0-4 weeks of storage for 'A-662CN' was 3.1 slightly better than 'Amoore Sweet' (3.0) and 'Bowden' (2.9) on a 5-point scale with 5 being exceptional storage.

Pit/stone:

*Size*.—Length 3.06 cm; diameter (midpoint) 2.16 cm.

*Shape*.—Oval with rough (furrowed and pitted) texture.

*Color*.—Greyed-orange group (167A).

*Tendency of pit to split*.—No split pits most years.

Kernel:

*Size*.—Length 1.58 cm; diameter 1.06 cm.

*Shape*.—Oval.

*Color*.—Greyed-orange group (163A).

Uses: Fresh consumption, not evaluated for drying or other uses.

THE CULTIVAR

The outstanding characteristics of 'A-662CN' are its early-season ripening, high soluble solids content, outstanding flavor, yellow, standard-acid, non-melting flesh, and moderate resistance to bacterial spot.

We claim:

1. A new and distinct cultivar of nectarine tree named 'A-662CN', substantially as illustrated and described.

* * * * *